United States Patent
Moriya

(10) Patent No.: US 8,164,749 B2
(45) Date of Patent: Apr. 24, 2012

(54) OPTICAL MEASUREMENT APPARATUS AND ELECTRODE PAIR THEREOF

(75) Inventor: Naoji Moriya, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 245 days.

(21) Appl. No.: 12/672,393

(22) PCT Filed: Aug. 8, 2007

(86) PCT No.: PCT/JP2007/065506
§ 371 (c)(1),
(2), (4) Date: Feb. 22, 2010

(87) PCT Pub. No.: WO2009/019766
PCT Pub. Date: Feb. 12, 2009

(65) Prior Publication Data
US 2010/0165342 A1 Jul. 1, 2010

(51) Int. Cl.
*G01N 21/00* (2006.01)
(52) U.S. Cl. ......... 356/336; 356/338; 204/547; 204/643
(58) Field of Classification Search .......... 356/335–343; 204/547, 643
See application file for complete search history.

(56) References Cited

U.S. PATENT DOCUMENTS

| | | | | |
|---|---|---|---|---|
| 5,094,532 A * | 3/1992 | Trainer et al. | ................. | 356/336 |
| 7,760,356 B2 * | 7/2010 | Moriya et al. | ................. | 356/336 |
| 7,911,610 B2 * | 3/2011 | Moriya et al. | ................. | 356/338 |
| 2009/0128809 A1 * | 5/2009 | Moriya | ................. | 356/335 |
| 2010/0012496 A1 * | 1/2010 | Tsunazawa et al. | ......... | 204/547 |
| 2010/0149532 A1 * | 6/2010 | Moriya | ................. | 356/336 |
| 2010/0177311 A1 * | 7/2010 | Wada | ................. | 356/336 |
| 2010/0231909 A1 * | 9/2010 | Trainer | ................. | 356/336 |

* cited by examiner

Primary Examiner — Hoa Pham
(74) Attorney, Agent, or Firm — Cheng Law Group, PLLC

(57) ABSTRACT

In an apparatus in which an electrode pair formed of two electrodes including multiple mutually parallel linear electrode pieces is provided in a container for storing particles dispersed movably in a medium to form an spatially regularly arranged electric field, the particles are migrated in the container due to the formation of the electric field by the application of a voltage to the electrode pair to generate a diffraction grating resulting from density distribution of the particles, diffracted light obtained by applying light to the diffraction grating is measured, and a particle size analysis or the like is performed from the temporal change in the diffracted light in the free diffusion process of the particles by stoppage or modulation of the application of the voltage, by making width L of the electrode pieces of the electrode pair and a space distance S between the electrode pieces as follows:

$L/(L+S) \leq 0.3$, steep attenuation of the diffracted light intensity is not generated at the initial stage of the diffusion of the particles to accurately measure the particle size distribution.

2 Claims, 14 Drawing Sheets

OPTICAL MEASUREMENT APPARATUS AND ELECTRODE PAIR THEREOF

TECHNICAL FIELD

The present invention relates to an apparatus for optically measuring information about the diffusion of particles in a sample having the particles dispersed movably in a medium and information about the particle size, the viscosity of the medium, and/or the migration of the particles and an electrode pair used in the apparatus, in particular, to an apparatus for forming periodic electric field distribution in a sample having particles dispersed movably in a medium to generate a diffraction grating resulting from density distribution of the particles and measuring information about the diffusion of the particles and information about the particle size, the viscosity of the medium, and/or the migration acting on the particles from the temporal change in the diffracted light from the diffraction grating and an electrode pair used in the apparatus to form electric field distribution in the sample.

BACKGROUND ART

Particles with a diameter of 100 nm or less are generally called nanoparticles, and are just beginning to be used in various fields because they have properties different from those of general bulk materials of even the same material. Various methods such as the laser diffraction/scattering method have been known as the method for measuring the particle size. Among them, methods based on the so-called dynamic scattering method (the photon correlation method) have been employed mainly for nanoparticles with a diameter of 100 nm or less (refer to Patent Literatures 1 and 2, for example).

The dynamic scattering method utilizes the Brownian motion of the particles. According to the method, particles performing a Brownian motion in a medium are exposed to a light beam, the intensity of scattered light from the particles is measured at a predetermined position, the fluctuation of the scattered light intensity caused by the Brownian motion of the particles, that is, the temporal change in the scattered light is captured, and the particle size distribution of the particles to be measured is calculated by utilizing the fact that particles each perform a Brownian motion with the intensity according to its particle size.

However, in the dynamic scattering method (the photon correlation method) in which the fluctuation of scattered light from the particles is measured, the fluctuation of the scattered light to be measured is imperceptible in the case of microparticles because the intensity of the scattered light from the microparticles is proportional to the fifth to sixth power of the particle size. Due to its principle, the problems of poor measurement sensitivity as well as poor S/N cannot be avoided.

As a powerful approach for solving such unavoidable problems in the dynamic scattering method, there has been proposed a method and an apparatus for electrophoresing particles dispersed movably in a medium by applying a spatially periodic electric field to the particles, generating a quasi-diffraction grating by making the particles have a spatially periodic alteration in concentration, in this state, detecting diffracted light obtained by exposing the particles to a parallel light flux such as a laser beam, and calculating the diffusion coefficient and the size of the particles from the temporal change in the diffracted light after stopping the application of the electric field (refer to Patent Literature 3).

The method and the apparatus proposed above utilize dielectrophoresis or electrophoresis of the particles in the medium, and utilizes the fact that, from the state where a diffraction grating resulting from concentration distribution (density distribution) of the particles is generated by applying an electric field, the annihilation process of the diffraction grating by stopping the application of the electric field depends on the diffusion coefficient of the particles. The diffusion coefficient and therefore the size of the particles can be calculated from the time required for dissipation of diffracted light from the diffraction grating resulting from density distribution of the particles.

In the measurement method and the apparatus described above, the diffraction grating resulting from the density distribution of the particles is formed in the vicinity of an electrode pair for applying the electric field to the sample to induce the dielectrophoresis of the particles. An electrode pattern with which diffracted light from the electrode pair and the diffracted light from the diffraction grating resulting from the density distribution of the particles can be separately measured is also proposed (refer to Patent Literature 4, for example).

That is, each of electrodes constituting the electrode pair includes multiple mutually parallel linear electrode pieces and a connection part electrically connecting the respective electrode pieces to each other. Each electrode has a pattern that electrode piece ununiformly-arranged areas including at least two linear electrode pieces arranged adjacently to each other, and electrode piece absent areas with no electrode piece arranged therein are formed alternately. The electrode pairs are formed by arranging the electrodes so that the electrode piece ununiformly-arranged areas of one electrode are positioned in the electrode piece absent areas of the other electrode respectively, and the electrode pieces are arranged in parallel with each other.

With the configuration above, when a voltage is applied to between the electrode pieces, high-density areas of the particles are formed only in a part where the electrode pieces of one electrode are adjacent to the electrode pieces of the other electrode. Thus, a grating pitch of the diffraction grating resulting from the density distribution of the particles is larger than a pitch of the electrode pieces. Thereby, the diffracted light of the specific order from the diffraction grating resulting from the density distribution of the particles, such as the diffracted light of the [2m+1]th order (m is an integer) in the case where two electrode pieces are ununiformly arranged in respective electrodes, has the outgoing direction which is different from that of the diffracted light from the diffraction grating formed by the electrode pieces. Thus, the diffracted light by the density distribution of the particles can be selectively detected.

In accordance with the method and the apparatus proposed above, the intensity of the diffracted light from the diffraction grating resulting from the concentration distribution of the particles is detected, and thus the intensity is greater than that of scattered light from particles obtained in the dynamic scattering method, thereby a more intense signal is to be measured, resulting in a significant improvement in S/N and sensitivity relative to the dynamic scattering method.

The present inventors clarified that calculation for obtaining information about the diffusion coefficient and information about the particle size and the like from the temporal change in the diffracted light measured by the method based on the proposals above can be extremely simplified and also the information can be accurately obtained (refer to Non-patent Literature 1, for example).

That is, assuming that I represents the diffracted light intensity in the annihilation process of the diffraction grating resulting from the density distribution of the particles, $I_0$ represents the starting value of the diffracted light intensity (immediately after the start of the annihilation), D represents the diffusion coefficient of the particles to be measured, and Λ represents the grating period, they are approximated by the following expressions (1) and (2).

[Mathematical Expression 1]

$$I = I_0 \exp(-2Dq^2 t) \quad (1)$$

[Mathematical Expression 2]

$$q = \frac{2\pi}{\Lambda} \quad (2)$$

The size "d" of the particles to be measured can be obtained from the following Einstein-Stokes relational expression using such diffusion coefficient D obtained from the measured value I of the diffracted light intensity in the annihilation process of the diffraction grating. The viscosity η of the medium can also be obtained by using particles whose particle size "d" is known.

[Mathematical Expression 3]

$$D = \frac{k_B T}{3\pi \eta d} \quad (3)$$

In the expression (3), $k_B$ is the Boltzmann constant, and T represents an absolute temperature.

Patent Literature 1: U.S. Pat. No. 5,094,532
Patent Literature 2: Japanese Patent Laid-Open Publication No. 2001-159595
Patent Literature 3: Japanese Patent Laid-Open Publication No. 2006-84207
Patent Literature 4: WO/2007/010639
Non Patent Literature 1: "Nanoparticle size analysis with relaxation of induced grating by dielectrophoresis" Yukihisa Wada, Shinichro Totoki, Masayuki Watanabe, Naoji Moriya, Yoshio Tsunazawa, and Haruo Shimaoka, OPTICS EXPRESS, 12 Jun. 2006/vol. 14, No. 12, pp 5755-5764

DISCLOSURE OF THE INVENTION

The Problems to be Solved by the Invention

With the electrode pair pattern described in Patent Literature 4 above, the diffracted light from the electrode pair and the diffracted light from the diffraction grating resulting from the density distribution of the particles can be surely separated. However, the sizes of the electrodes, specifically width L of the linear electrode pieces and a space distance S between the adjacent electrode pieces are not at all known. In the figures, the sizes L and S are shown as substantially similar sizes, that is, L/(L+S)=0.5.

In Non-patent Literature 1, the sizes of the electrodes are clearly described as L/(L+S)=0.5. By using such an electrode pair pattern, a voltage is applied to between the electrodes of the electrode pair to cause the migration of the particles and the diffraction grating resulting from the density distribution of the particles is generated. After that, when the application of the voltage is stopped to freely diffuse the particles and the temporal change in the diffracted light intensity in the process of annihilating the diffraction grating is measured, steep attenuation of the diffracted light intensity is slightly observed at the initial stage of the diffusion (this is clearly seen in measurement results of the particles with a diameter of 5 nm shown in FIG. 7 of Non-patent Literature 1). As discussed in Non-patent Literature 1, such steep attenuation of the diffracted light intensity at the initial stage is assumed to be from the expressions (10) and (11) thereof or the like even in the measurement of the particles with a single diameter. Assuming that the analytical expressions are right with sufficient accuracy, it is predicted that the initial attenuation above would differently act according to a complex refraction index of the particles. It is thought that steep attenuation of the diffracted light intensity is observed at the initial stage with the absorption coefficient of zero as shown in FIG. 5 of Non-patent Literature 1.

Meanwhile, the same phenomenon is also generated in the case where particles with a smaller diameter exist in particles with a diameter calculated from the attenuation of the diffracted light intensity observed at the intermediate stage of the diffusion. Therefore, when the particles have particle size distribution, it is difficult to perform an accurate analysis. FIG. 22 shows a measurement example regarding to polystyrene particles with a diameter of 60 nm. In FIG. 22, the horizontal axis indicates the time, the vertical axis indicates the diffracted light intensity by an exponential function, a solid line indicates an actually measured value, and a broken line indicates a calculated value by the theory approximation expression. FIG. 22 clearly shows that the actually measured value is deviated from the value calculated by using the theory approximation expression for about a little more than 2 seconds at the initial stage of the diffusion. This indicates that the particle size cannot be analyzed by using the theory approximation expression for about 3 seconds at the initial stage of the diffusion, in the case where a sample including particles with the maximum diameter of 60 nm is measured for example.

Next, FIG. 23 is a graph showing, in a superimposed state, an actually measured value (a solid line) of the temporal change in the diffracted light intensity in the case where the particles with a diameter of 10 nm are included by an equal amount to the particles with a diameter of 60 nm, and a calculated value (a broken line) obtained by the theory approximation expression in the case where the attenuation rate of the diffracted light after 3 seconds passes from the start of the diffusion is substantially similar with the measured values, that is, a rate of 0.49 of the particles with a diameter of 60 nm and a rate of 0.16 of the particles with a diameter of 20 nm are included. As shown in the figure, it is extremely difficult to discriminate the two different mixed samples from the inclination of the attenuation of the diffracted light after about 3 seconds passes from the start of counting.

The present invention is achieved in consideration with such a situation, and an object thereof is to provide an optical measurement apparatus capable of accurately measuring particle size distribution even for particles to be measured with arbitrary size distribution, and an electrode pair thereof.

Means for Solving the Problems

In order to solve the problems above, an optical measurement apparatus according to the present invention includes: a container for storing a sample having particles dispersed movably in a medium; a power source for generating an AC or DC voltage; an electrode pair for generating an electric field having a space period in the container by application of the voltage from the power source; an irradiation optical system for applying a parallel light flux to a diffraction grating resulting from density distribution of the particles generated in the container by the application of the voltage; a detection optical system for detecting diffracted light generated from the parallel light flux passing through the diffraction grating; voltage control means for controlling to generate and annihilate the diffraction grating resulting from the density distribution of the particles in the container by the application of the voltage from the power source to the electrode pair and stoppage and modulation of the application of the voltage; and data processing means for taking in outputs of the detection optical system to execute the process of evaluating characteristics of the particles and/or the medium. In the optical measurement apparatus, electrodes constituting the electrode pair include multiple mutually parallel linear electrode pieces and a connection part electrically connecting the respective electrode pieces to each other, respectively, electrode piece ununiformly-arranged areas including at least two of the linear electrode pieces arranged adjacently to each other, and electrode piece absent areas without the electrode pieces arranged therein are alternately formed in each of the electrodes, the electrodes are arranged so that the electrode piece ununiformly-arranged areas of one of the electrodes are positioned in the electrode piece absent areas of the other electrode, and the electrode pieces of the electrodes are in parallel with each other at regular intervals, and a relationship between width L of the electrode pieces of each of the electrodes and a space distance S between the electrode pieces is as follows:

$L/(L+S) \leq 0.3$.

The electrode pair according to the present invention is used in the optical measurement apparatus above, and has the pattern and the dimensional ratio described above. The electrode pair is formed of a vapor deposition film of a conductive body on a surface of a transparent flat plate.

The present invention is achieved as a result of earnestly examining the cause of a steep decrease in the diffracted light intensity at the beginning of the start of the diffusion of the particles by the stoppage or the modulation of the application of the electric field after generating the diffraction grating resulting from the particles. Hereinafter, an action based on the configuration of the present invention will be described with the process of reaching to the configuration.

Firstly, by numerically simulating the temporal change in the diffracted light intensity based on the Fraunhofer diffraction theory, a relationship between an electrode shape and a profile of the attenuation of the diffracted light was simulated. FIG. 9 shows a profile of particle density (concentration) used in the simulation. In FIG. 9, the horizontal axis indicates a position (the grating pitch direction) by the unit of m, and the vertical axis indicates particle concentration with one serving as 100%. The amplitude of phase modulation and the transmission amplitude by the particles are respectively set to be 0.01 and 0.0002 proportional to the profile of the particle density. As shown in the figure, the profile of the particle density is such that width of the high-density areas of the particles is 5 μm, and a space between the high-density areas is 15 μm (the grating pitch is 20 μm).

FIG. 10 shows simulation results of the attenuation of the diffracted light without the electrodes, that is, the temporal change in the diffracted light intensity when the particles are freely diffused after the generation of the diffraction grating resulting from the density distribution of the particles. The horizontal axis indicates the time, and the vertical axis indicates the diffracted light intensity which is displayed as logarithm and is a value normalized with using the diffracted light intensity immediately before the start of the diffusion as one. The calculation is performed with a diameter of the particles of 60 nm, the medium of water, and a temperature of 25° C. The calculation is performed to obtain a ratio showing how the attenuation coefficient of the diffracted light is different from the following exponential function which is the theory approximation expression:

[Expression 4]

$$\exp[-2q^2 Dt] \qquad (4)$$

FIG. 11 shows results of the calculation. In FIG. 11, the horizontal axis indicates the time, and the vertical axis indicates a coincidence index with the exponential function by the expression (4), which is as shown below:

[Expression 5]

$$\frac{I(t+\delta t) - I(t)}{\exp[-2q^2 D\{t+\delta t\}] - \exp[-2q^2 Dt]} \qquad (5)$$

FIG. 11 shows that the attenuation of the diffracted light almost corresponds to the theory approximation expression over the entire calculation time.

Next, the electrode pair is provided and then the calculation is performed. At the time, the width of the multiple electrode pieces constituting the electrode pair is set to be 5 μm, and the space between the electrode pieces is set to be 5 μm. Then, the calculation of the diffracted light in the case where the high-density areas of the density distribution of the particles in FIG. 9 correspond to the space between the electrodes is performed. This corresponds to a schematic profile of particle distribution in the case where the particles are collected due to the electric migration to generate the diffraction grating by the electrode pair configuration described in Patent Literature 4 above, that is, the electrode pair with the pattern with which the electrode piece ununiformly-arranged areas of one electrode which include the two electrode pieces adjacently arranged are fitted into the electrode piece absent areas of the other electrode without electrode pieces arranged therein.

FIG. 12 shows the attenuation of the diffracted light, and FIG. 13 shows the coincidence index with the exponential function serving as the theory approximation expression. FIG. 13 clearly shows that by adding the electrode pair with the shape and the size described above, the inclination is increased more than the exponential function predicted from the theory at the initial stage of the diffusion, that is, the diffracted light intensity is steeply attenuated at the initial stage of the diffusion.

FIGS. 12 and 13 are almost similar to FIGS. 10 and 11 except that an influence of the electrodes is taken into consideration or not. Basically, the figures show that steep attenuation at the initial stage of the diffusion is generated by the existence of the electrode pair with the width of the electrode pieces of 5 μm, and the space between the electrode pieces of 5 μm.

Next, in order to examine whether or not the existence of the electrodes itself is the cause of steep attenuation of the diffracted light described above, same profile of the particle density as in FIG. 9 is used for the calculation, but only the electrode pattern is changed, that is, the width of the electrode pieces is 1 μm and the space between the electrode pieces is 9 μm. FIG. 14 is a graph showing the transmission by the electrode pattern, FIG. 15 is a graph showing the attenuation of the diffracted light, and further FIG. 16 is a graph showing the coincidence index with the exponential function serving as the theory approximation expression described above. The figures clearly show that the existence of the electrodes itself is not the cause of steep attenuation described above.

However, in the case of the electrode pattern with the width of the electrode pieces of 1 μm and the space between the electrode pieces of 9 μm, the profile of the particle density is originally to be different from the profile of FIG. 9, and the high-density areas of the particles are to be formed in the entire space between the electrode pieces.

The profile of the particle density is changed to the profile of FIG. 17, and the calculation is firstly performed for the case where the electrodes do not exist. FIG. 18 shows the profile of the attenuation of the diffracted light, and FIG. 19 shows the coincidence index with the exponential function serving as the theory approximation expression. FIG. 19 shows that the attenuation of the diffracted light well corresponding to the exponential function of the theory approximation expression can be obtained with the profile of the particle density of FIG. 17.

Next, the electrode pattern shown in FIG. 14, that is, the electrode pattern with the width of the electrode pieces of 1 μm and the space distance between the electrode pieces of 9 μm is added to the profile of the particle density shown in FIG. 17 to perform the calculation of the diffracted light. FIG. 20 shows the profile of the attenuation of the diffracted light, and FIG. 21 shows the coincidence index with the exponential function serving as the theory approximation expression. The figures clearly show that the attenuation of the diffracted light well corresponds to the exponential function of the theory approximation expression irrespective of the existence of the electrodes.

Thus, it is found that when the width of the electrode pieces is expressed as L and the space between the electrode pieces is expressed as S in the electrode pair pattern for evoking the diffraction grating resulting from the density distribution of the particles, there is a range where the attenuation of the diffracted light is regarded as substantially the same as the exponential function when "L/(L+S)" is equal to a value from 0.1 to 0.5.

It should be noted that the finding above is only the investigation based on the numerical calculation, and thus there is a possibility that different results may be obtained due to an error of the numerical calculation or according to actual distribution of particle collection. Therefore, as will be described later, electrode pairs with various widths of electrode pieces and various space distances between the electrode pieces were actually produced and experiments were performed by using actual samples having particles dispersed in mediums. Thereby, the simulation results above were examined to explore an electrode pair pattern capable of solving the problems. As a result, it was confirmed that by making a relationship between width L of the electrode pieces of electrodes constituting the electrode pair and a space distance S between the electrode pieces as follows:

$$L/(L+S) \leq 0.3,$$

the attenuation rate of the diffracted light corresponds to the theory approximation expression.

By using the electrode pair with such a pattern, the particle size distribution analysis can be performed even for a sample in which particles having a plurality of size are mixed.

Figure 1:
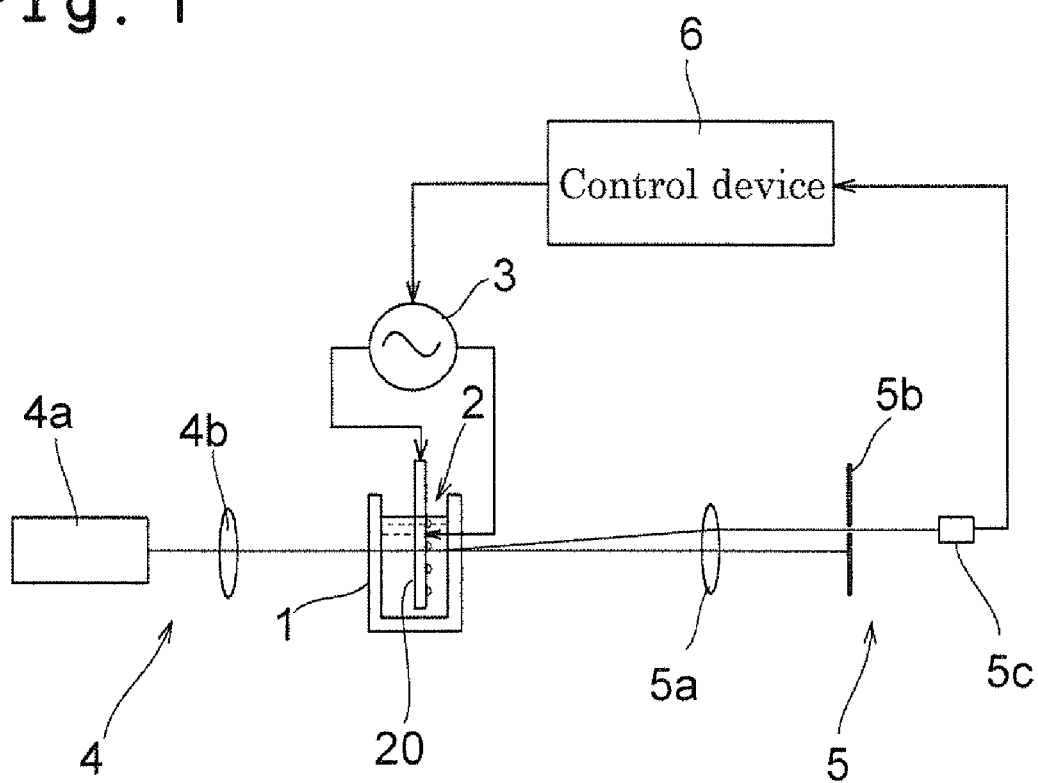
FIG. 1 is a configuration diagram of an embodiment of the present invention including a schematic diagram showing an optical arrangement and a block diagram showing an electric arrangement.

| Reference Numerals | |
|---|---|
| 1 | Sample cuvette |
| 2 | Electrode pair |
| 21, 22 | Electrodes |
| 21a, 22a | Electrode pieces |
| 21b, 22b | Connection parts |
| 3 | Power source |
| 4 | Irradiation optical system |
| 5 | Detection optical system |
| 6 | Data processing and control section |
| P | High-density areas of particles |

BEST MODE FOR CARRYING OUT THE INVENTION

An embodiment of the present invention will hereinafter be described with reference to the accompanying drawings.

Figure 2:
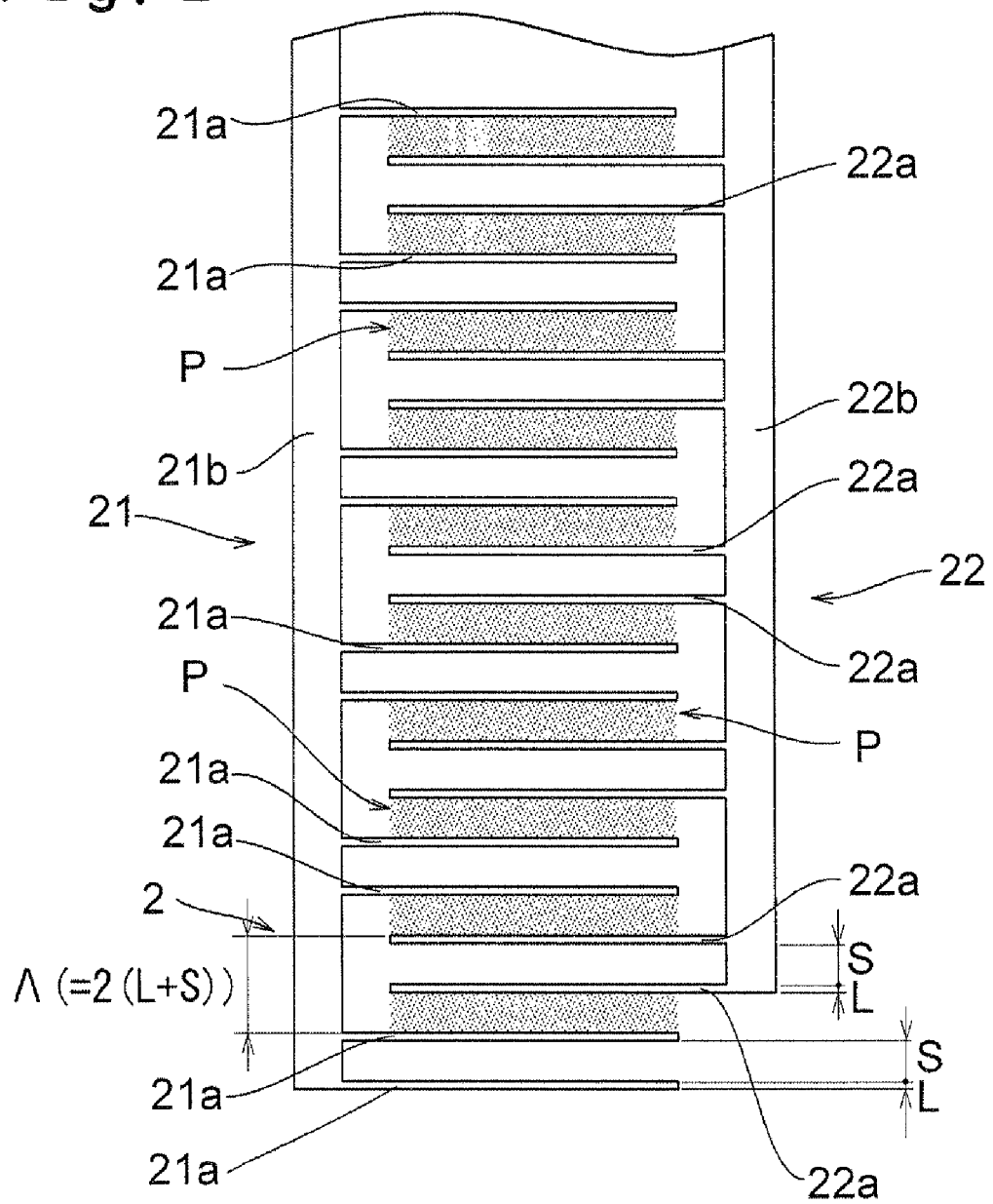
FIG. 2 is a diagram showing an electrode pair pattern in the embodiment of FIG. 1.

FIG. 1 shows an overall configuration of an optical measurement apparatus to which the present invention is applied, and FIG. 2 shows a pattern example of an electrode pair 2 arranged in a sample cuvette 1.

The apparatus includes mainly: a sample cuvette 1 for storing a sample having particles dispersed movably in a medium, for example, a sample having particles dispersed in a liquid, or a sample composed of a gel having particles dispersed movably therein; an electrode power source 3 for applying a voltage to an electrode pair 2 provided in the sample cuvette 1; an irradiation optical system 4 for applying light to the sample cuvette 1; a detection optical system 5 for measuring diffracted light from a diffraction grating resulting from density distribution of the particles generated in the sample cuvette 1 through the application of a voltage to the electrode pair 2; and a data processing and control section 6 for collecting outputs from the detection optical system 5 to perform various analyses as well as for controlling the measuring operations of the apparatus.

The sample cuvette 1 is composed of a transparent material such as glass, in which a plate-like member 20 also composed of a transparent material is arranged fixedly, and the electrode pair 2 is formed on the surface of the plate-like member 20.

As shown in FIG. 2, the electrode pair 2 includes comb-like electrodes 21 and 22, and the electrodes 21 and 22 have multiple mutually parallel linear electrode pieces 21a . . . 21a and 22a . . . 22a and connection parts 21b and 22b electrically connecting the respective electrode pieces 21a . . . 21a and 22a . . . 22a to each other, respectively.

The electrodes 21 and 22 each have a shape in which electrode piece ununiformly-arranged areas including two linear electrode pieces 21a or 22a arranged adjacently to each other and electrode piece absent areas with no electrode piece arranged therein are formed alternately. Then, two electrode pieces 21a or 22a in each electrode piece ununiformly-arranged area of one electrode are fitted into each electrode piece absent area of the other and, as a whole, the electrode pieces 21a and 22a are arranged alternately two by two in parallel with each other at regular intervals. The electrode pair 2 is formed by vapor deposition of a conductive body such as metal.

A relationship between width L of the electrode pieces 21a and 22a of the electrodes 21 and 22 and a space distance S between the adjacent electrode pieces 21a or 22a is as follows:

$$L/(L+S) \leq 0.3$$

When a voltage is applied from the power source 3 to the electrode pair 2, electric field distribution is generated in the sample stored in the sample cuvette 1, and the particles in the sample are migrated due to the electric field distribution as will be described hereinafter, thereby a diffraction grating resulting from the density distribution of the particles is generated. In this example, the power source 3 is an AC power source, and the particles are moved by the dielectrophoretic force.

The irradiation optical system 4 outputs substantially monochromatic light shaped into a substantially parallel light flux, and the output light is applied to the electrode pair 2 in the sample cuvette 1. As a light source of the irradiation optical system 4, an element that emits only monochromic light such as a laser or an LED is easy to use. However, a continuous wavelength light source can also be used, if the light thereof is made quasi-monochromic through a band pass filter, a spectrometer or the like. The spectrum bandwidth may be about tens nm or less, for example, within the visible wavelength range. In this example, the irradiation optical system 4 includes a laser 4a and a collimation lens 4b.

The detection optical system 5 is arranged in the outgoing direction of, for example, diffracted light of the first order diffracted by a diffraction grating resulting from the density distribution of the particles in the sample cuvette 1 of the light from the irradiation optical system 4. The detection optical system 5 includes, for example, a condenser lens 5a, a pinhole 5b, and a light detector 5c. The detection optical system 5 measures the temporal change in the intensity of diffracted light from the diffraction grating resulting from the density distribution of the particles in the sample cuvette 1.

In the above-described arrangement, when an AC voltage from the power source 3 is applied to between the electrodes 21 and 22 constituting the electrode pair 2, electric field distribution according to the electrode pattern is formed in the sample within the sample cuvette 1, and density distribution of the particles is caused by dielectrophoresis based on the electric field distribution. That is, in the electrode pair 2 shown in FIG. 2, high-density areas P of the particles are formed in a part where electrode pieces of reverse polarities are adjacent to each other, or in a part where the electrode pieces 21a of one electrode 21 are adjacent to the electrode pieces 22a of the other electrode 22 as shown in FIG. 2. The high-density areas P of the particles are formed in a spatially repeated manner at the pitch which is twice the arrangement pitch of the electrode pieces 21a or 22a, and in parallel with the electrode pieces 21a and 22a. And a diffraction grating is formed by the multiple high-density areas P of the particles. When the application of the voltage to the electrode pair 2 is stopped in the state where the diffraction grating exists, the particles start to be diffused and thereby the spatial density of the particles in the sample becomes uniform, and accordingly the diffraction grating resulting from the density distribution of the particles is annihilated in due course.

When the parallel light fluxes from the irradiation optical system 4 are applied to the diffraction grating resulting from the density distribution of the particles, the light is diffracted by the diffraction grating. In the electrode pattern shown in FIG. 2, the diffraction grating resulting from the density distribution of the particles has a grating pitch twice as large as that of a diffraction grating formed by the electrode pieces 21a and 22a, so that the grating constants are different between the diffraction gratings. Therefore, since the diffracted light from the diffraction grating resulting from the density distribution of the particles and diffracted light from the diffraction grating formed by the electrode pieces 21a and 22a appear in their respective different directions, only the diffracted light from the diffraction grating resulting from the density distribution of the particles can be detected by arranging the pinhole 5a and light detector 5b at required positions.

Figure 3:
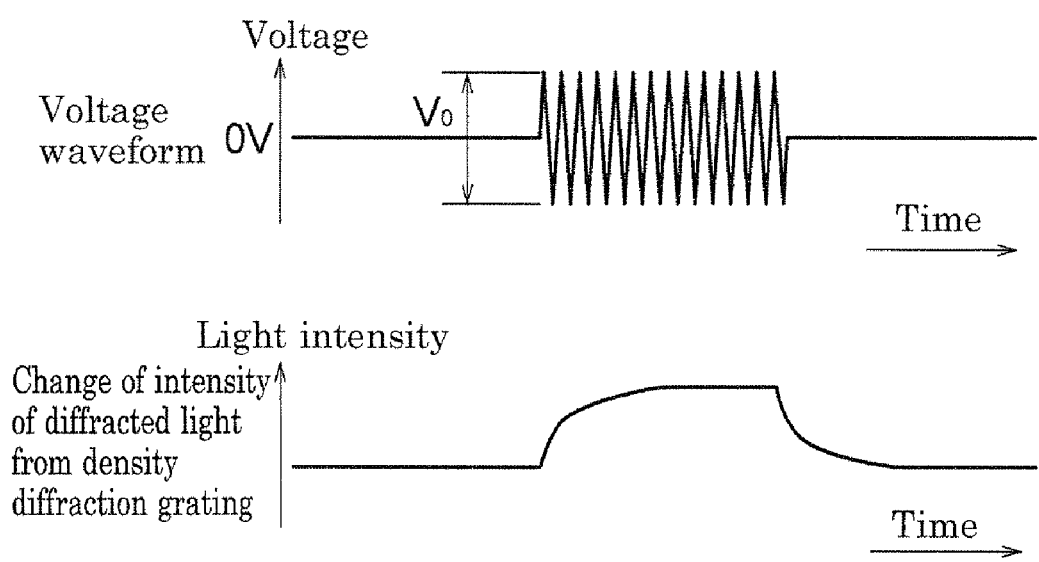
FIG. 3 is a graph showing an example of a voltage waveform applied to an electrode pair and an example of the temporal change in the intensity of diffracted light from a diffraction grating resulting from density distribution of particles at the time of measurement in the embodiment of FIG. 1.

The intensity of the thus detected diffracted light from the diffraction grating resulting from the density distribution of the particles gradually decreases during the process of annihilation of the diffraction grating. FIG. 3 is a graph showing an example of a voltage waveform applied to the electrode pair 2 and an example of the temporal change in the intensity of diffracted light from the diffraction grating resulting from the density distribution of the particles. These examples show the case where a constant sinusoidal AC voltage $V_0$ is applied to the electrode pair 2 to cause a dielectrophoretic force to operate on the particles.

When the relationship between the width L of the electrode pieces 21a and 22a and the space distance S between the electrode pieces 21a or 22a is set within the range as described above, steep attenuation of the diffracted light intensity is not observed at the initial stage of the diffusion of the particles. Thereby, the size distribution of the particles can be accurately calculated.

In order to prove this, the following experiments were performed. "Electrode piece width L/space distance S" is used as the relationship between the width L of the electrode pieces 21a and 22a of the electrodes 21 and 22 constituting the electrode pair 2 and the space distance S between the adjacent electrode pieces 21a or 22a, and electrode pairs having following values of "electrode piece width L/space distance S between the electrode pieces" were actually produced: (a) 1 μm/10 μm; (b) 3 μm/10 μm; (c) 10 μm/10 μm; and (d) 3 μm/7 μm. The value of L/(L+S) is about 0.09 in case of the electrode pair (a), about 0.23 in case of the electrode pair (b), 0.50 in case of the electrode pair (c), and 0.30 in case of the electrode pair (d).

The electrode pairs above were used as the electrode pair 2 of the apparatus shown in FIG. 1, and a sample having polystyrene particles with a diameter of 60 nm serving as particles to be measured dispersed in water was stored in the sample cuvette 1. After the diffraction grating resulting from the particles was generated by the application of a voltage to the electrode pair 2, the application of the voltage was stopped to disperse the particles. The temporal change (the attenuation) in the diffracted light intensity in the dispersion process was measured.

Figure 4:
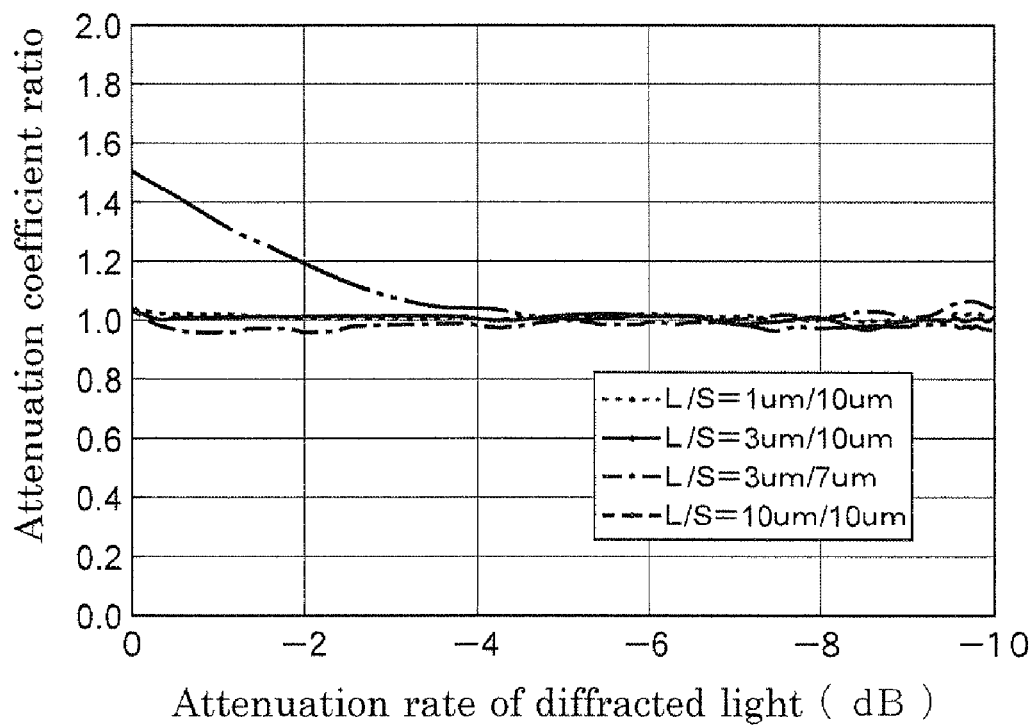
FIG. 4 is a graph showing results of experiments performed by using variously different width of the electrode pieces of the electrode pair and space distances between the electrode pieces in the embodiment of FIG. 1, and the graph showing the attenuation coefficient ratio obtained by calculating attenuation coefficients at multiple attenuation points relative to an average attenuation coefficient $\Gamma_0(=2q^2D)$ at the late stage of attenuation of the diffracted light for the respective electrode pairs.

With regard to measurement results of the diffracted light intensity using the electrode pairs above, attenuation coefficients at multiple attenuation points relative to an average attenuation coefficient $\Gamma_0 (=2q^2 D)$ at the late stage of the attenuation of the diffracted light were calculated, and the values were defined as the attenuation coefficient ratio. Calculation results thereof are shown in the graph of FIG. 4. In FIG. 4, the horizontal axis indicates the attenuation rate of the diffracted light by the unit of dB, and the vertical axis indicates the index number which is normalized with using the value of the average attenuation coefficient which is average of the attenuation coefficient from the point that the diffracted light intensity is attenuated by −3 dB (that is, one half) from the intensity immediately after the diffusion to the point attenuated by −10 dB (one tenth) therefrom, as one.

As shown in FIG. 4, in case of the electrode pair with "electrode piece width L/space distance S between the electrode pieces" of 10 μm/10 μm, the attenuation coefficient largely varies in a region where the diffracted light is attenuated by −5 dB from the initial intensity. Meanwhile, the attenuation coefficient is substantially constant in case of the electrode pairs of 1 μm/10 μm and 3 μm/10 μm. In case of the electrode pair of 3 μm/7 μm, it can be said that the attenuation coefficient is substantially constant except slight variation at the very initial stage. This demonstrates that in case of at least $L/(L+S) \leq 0.3$, the attenuation rate of the diffracted light corresponds to the theory approximation expression. Therefore, when using an electrode pair with a pattern having such a size relationship, an accurate particle size distribution analysis can be performed when measuring particles having a plurality of sizes.

Figure 5:
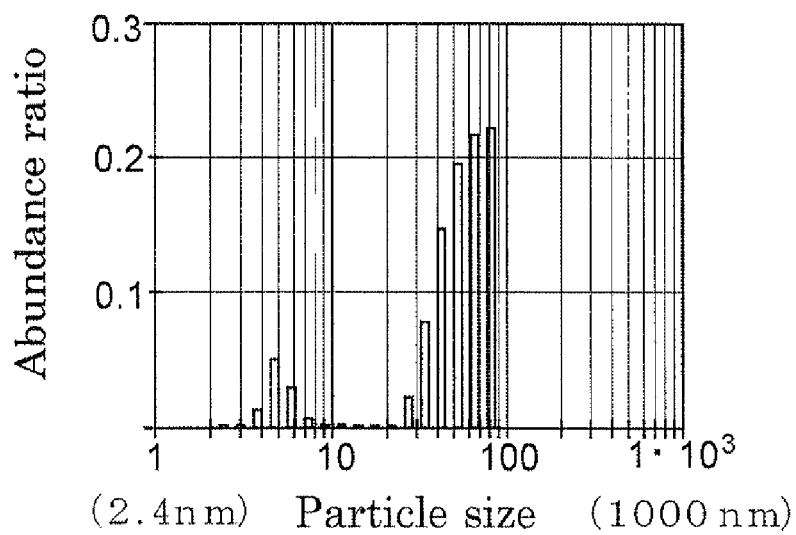
FIG. 5 is a graph showing results of a particle size analysis with using measured data of the diffracted light using the electrode pair with L/S of 10 μm/10 μm among the electrode pairs shown in FIG. 4.
Figure 6:
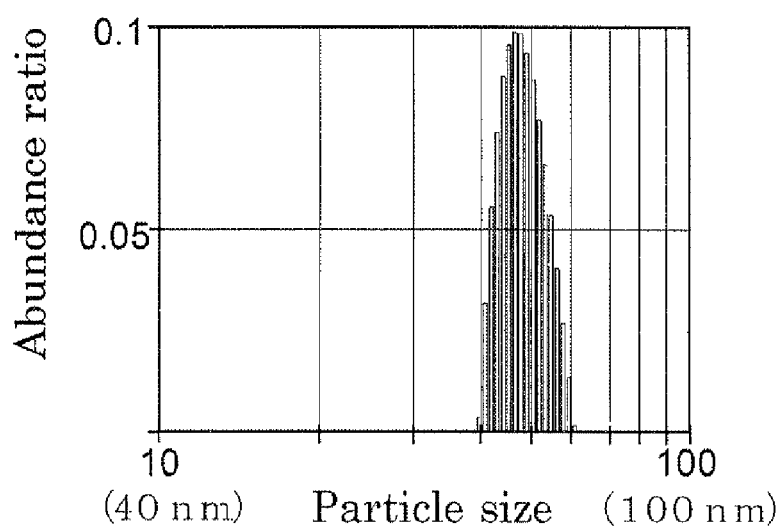
FIG. 6 is a graph showing results of the particle size analysis with using measured data of the diffracted light using the electrode pair with L/S of 1 μm/10 μm among the electrode pairs shown in FIG. 4.

Next, for further confirming the above, the particle size analysis was performed with using the measurement results of the temporal change in the diffracted light in the case where the electrode pairs with L/S of 1 μm/10 μm and 10 μm/10 μm among the electrode pairs shown in FIG. 4 were used. FIG. 5 shows results of the particle size analysis with using measured data of the diffracted light using the electrode pair with L/S of 10 μm/10 μm, and FIG. 6 shows results of the particle size analysis with using measured data of the diffracted light using the electrode pair with L/S of 1 μm/10 μm. In the analyses, the particle size was divided into seventeen channels and the NNLS (Non Negative Least Square) method was used for the distribution analysis.

The particles to be measured are polystyrene particles with a diameter of 60 nm as described above. In the analytical results of the data using the electrode pair of 10 μm/10 μm, steep attenuation of the diffracted light at the initial stage of the diffusion of the particles is reflected in the analysis result which looks as if small particles exist, and as if large size distribution of the particles is suddenly broken off in the distribution in the vicinity of the original particle size. That is, the result shows physically improbable distribution. Meanwhile, in case of the electrode pair of 1 μm/10 μm, the result shows the particle size distribution of a normal distribution, and namely rational analytical results are obtained.

Figure 7:
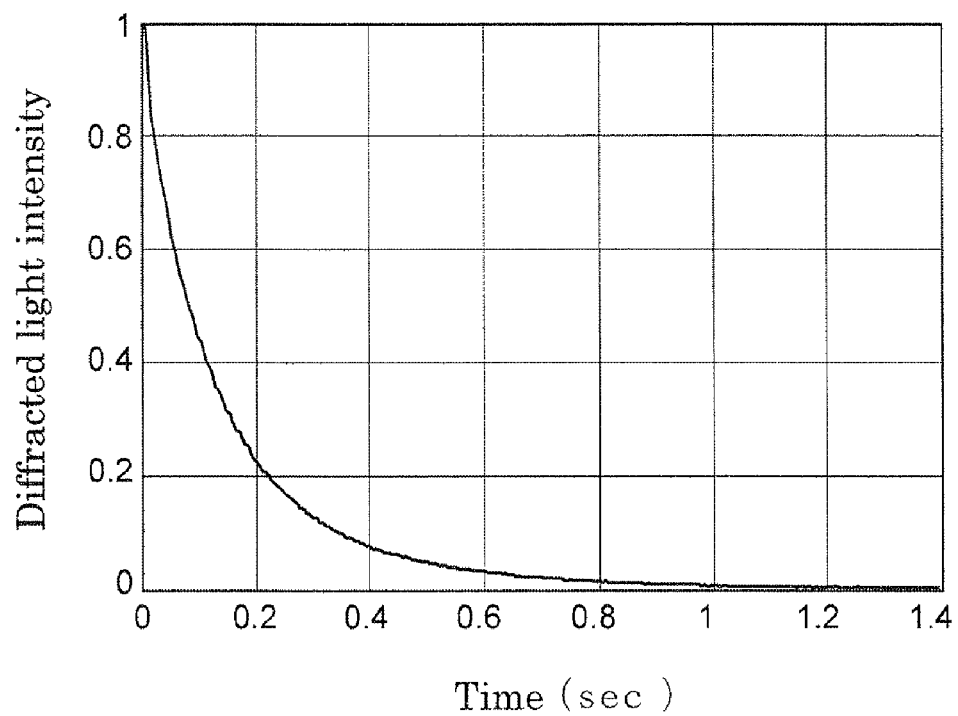
FIG. 7 is a graph showing measurement results of the temporal change in the diffracted light obtained when mixed particles having peaks in multiple sizes are measured using the electrode pair with L/S of 1 μm/9 μm.

Next, with using the electrode pair with L/S of 1 μm/9 μm separately from the electrode pairs described above, experiments for measuring mixed particles having peaks in multiple size were performed. FIG. 7 shows measurement results of the temporal change in the diffracted light intensity in the diffusion process of the particles, and FIG. 8 shows results of the particle size analysis which the measurement results were divided into the particle size of seventeen channels by the NNLS method as well as the analysis above.

Figure 8:
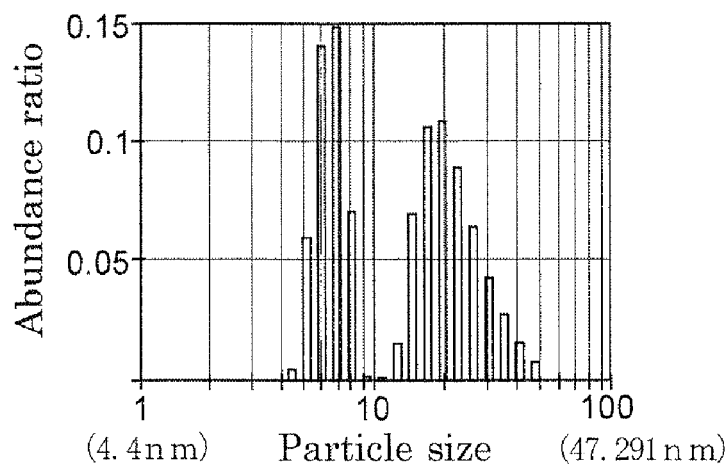
FIG. 8 is a graph showing calculation results of particle size distribution obtained by performing the particle size analysis for the measurement results of FIG. 7.
Figure 9:
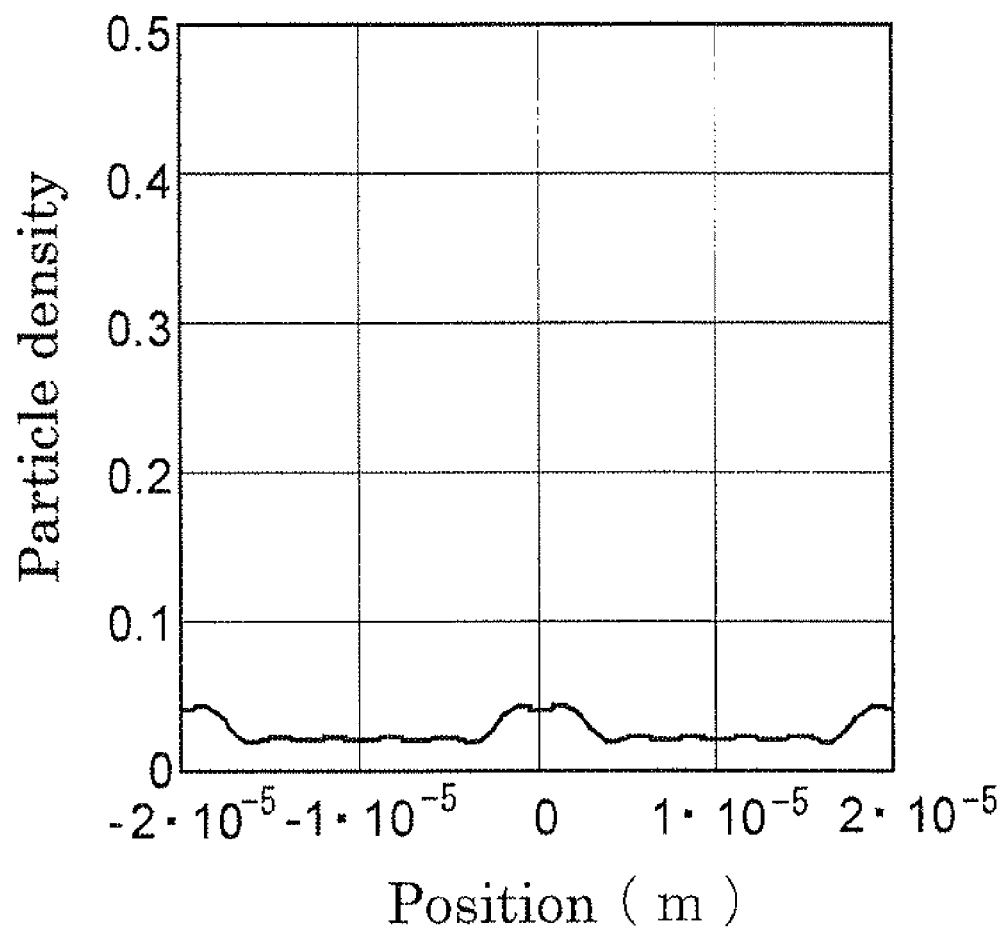
FIG. 9 is a graph showing a profile of particle density used in numerical simulation of the temporal change in the diffracted light intensity.
Figure 10:
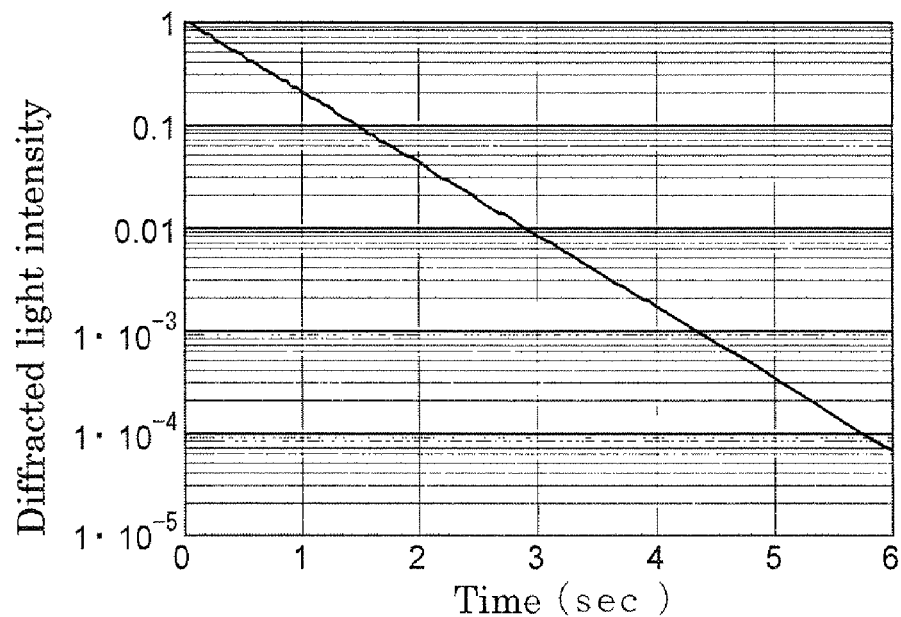
FIG. 10 is a graph showing simulation results of the temporal change in the diffracted light intensity when the particles are freely diffused from the profile of the particle density shown in FIG. 9 in which no electrodes exist.
Figure 11:
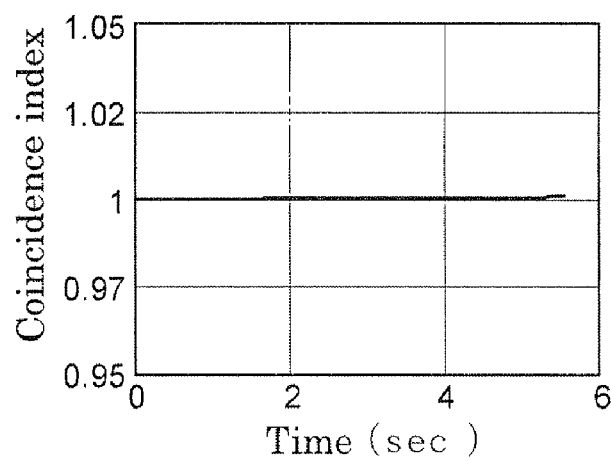
FIG. 11 is a graph showing a coincidence index between the simulation results of FIG. 10 and the theory approximation expression.
Figure 12:
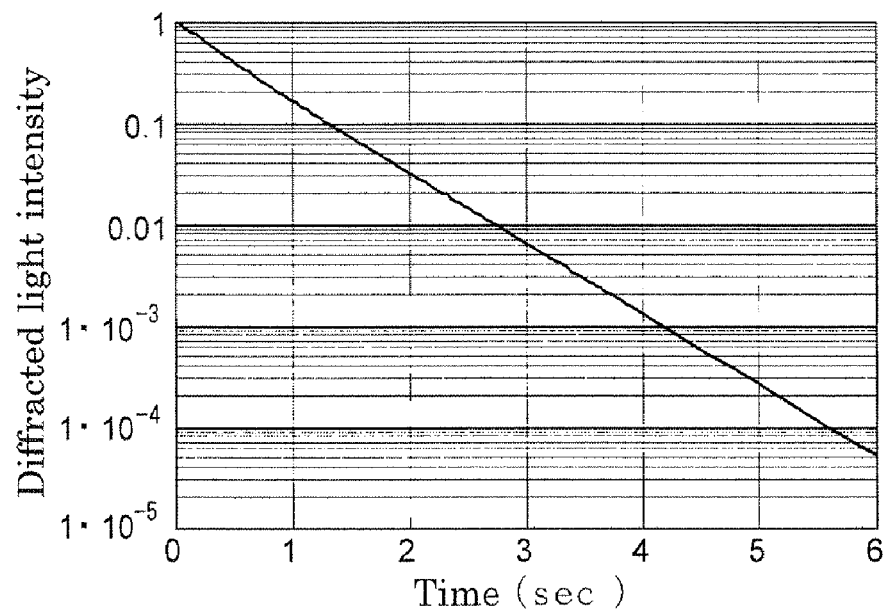
FIG. 12 is a graph showing simulation results of the temporal change in the diffracted light intensity when the particles are freely diffused from the profile of the particle density shown in FIG. 9 to which the electrodes with the width of the electrode pieces of 5 μm and the space between the electrode pieces of 5 μm are added.
Figure 13:
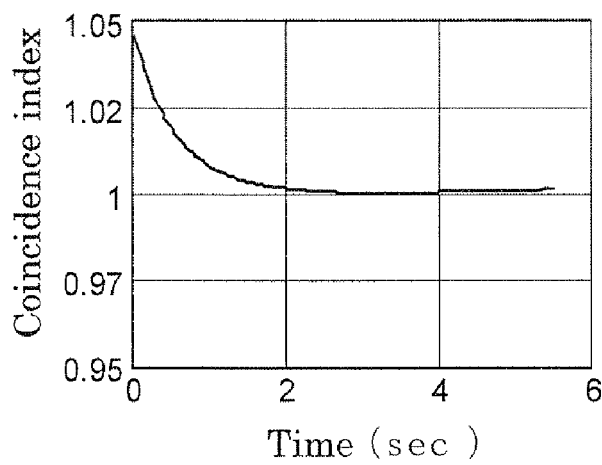
FIG. 13 is a graph showing the coincidence index between the simulation results of FIG. 12 and the theory approximation expression.
Figure 14:
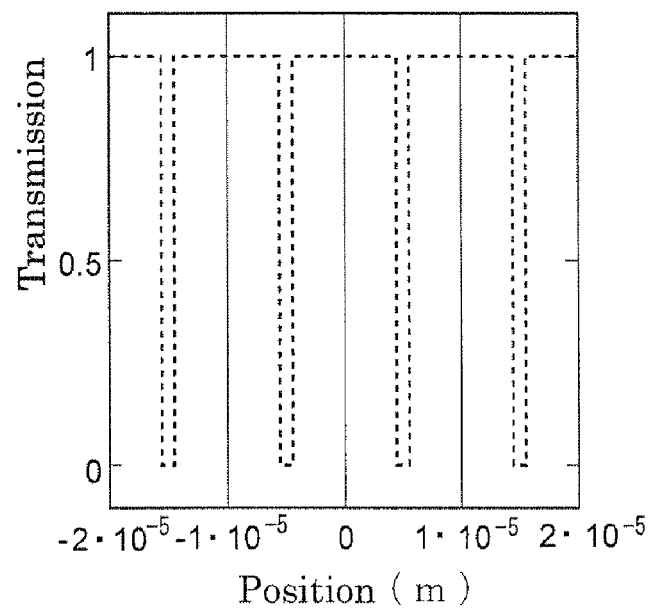
FIG. 14 is a graph showing the transmission of an electrode pattern of electrodes used when adding electrodes having the other pattern from the simulation of FIG. 12.
Figure 15:
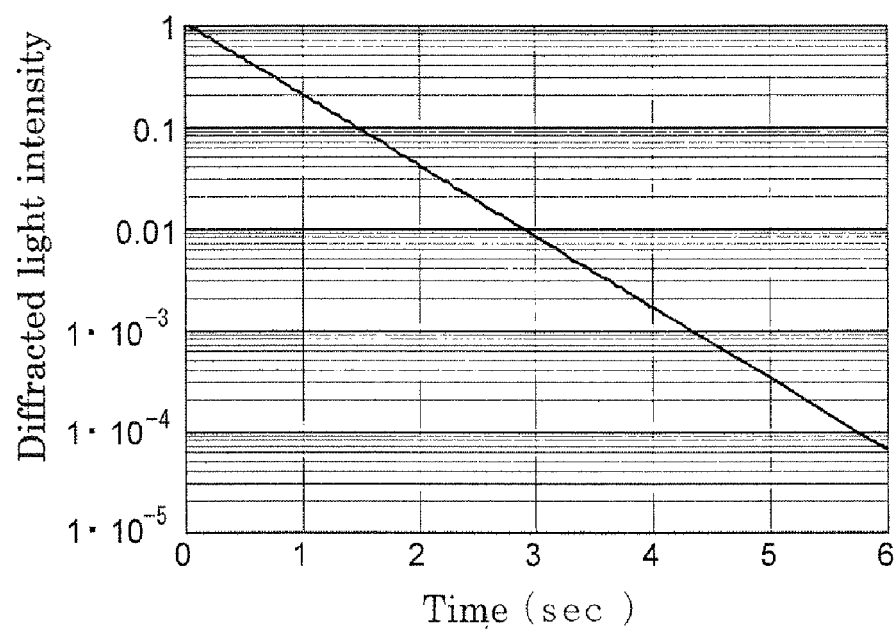
FIG. 15 is a graph showing simulation results of the temporal change in the diffracted light intensity when the particles are freely diffused from the profile of the particle density shown in FIG. 9 to which the electrodes of FIG. 14 are added.
Figure 16:
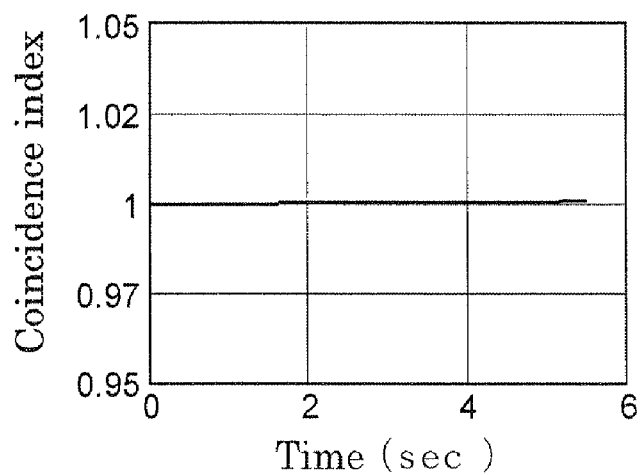
FIG. 16 is a graph showing the coincidence index between the simulation results of FIG. 15 and the theory approximation expression.
Figure 17:
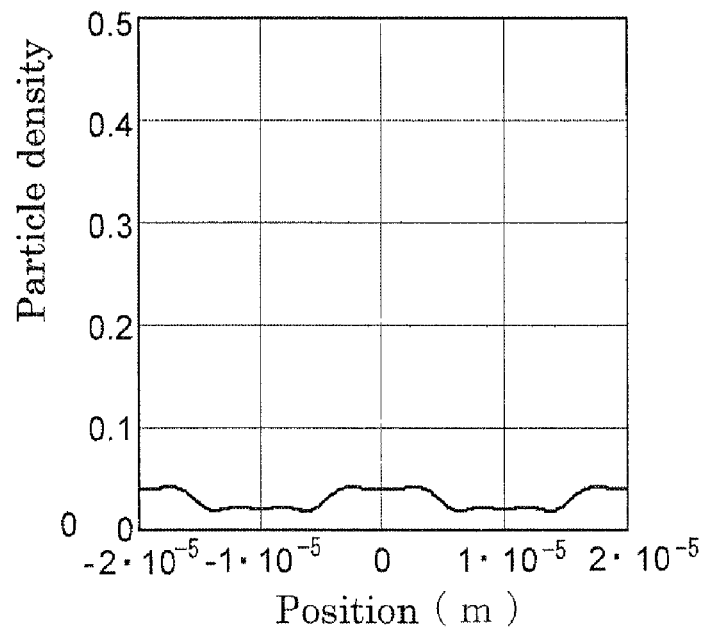
FIG. 17 is a graph showing a profile of the particle density corresponding to the electrode pattern of FIG. 14.
Figure 18:
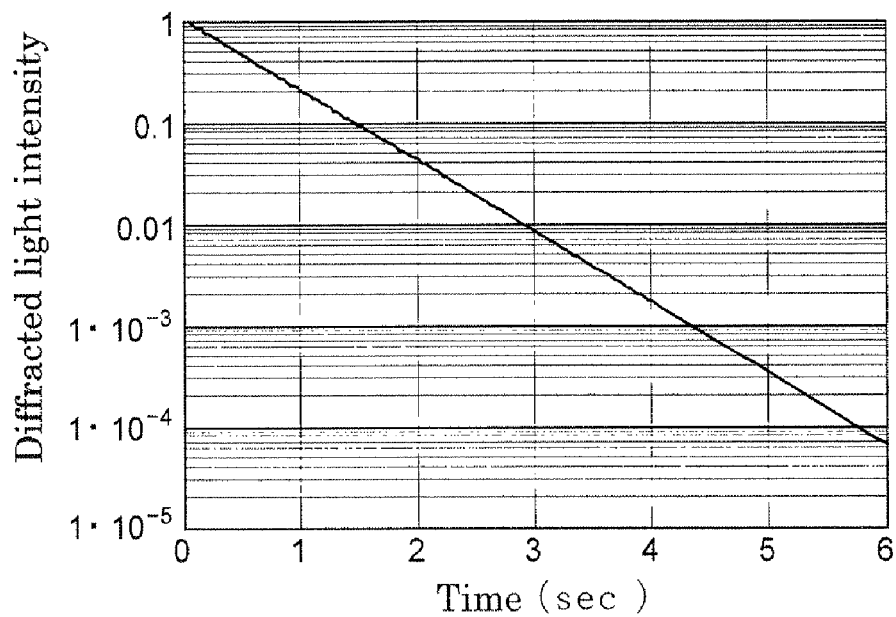
FIG. 18 is a graph showing simulation results of the temporal change in the diffracted light intensity when the particles are freely diffused from the profile of the particle density of FIG. 17 in which no electrode pieces exist.
Figure 19:
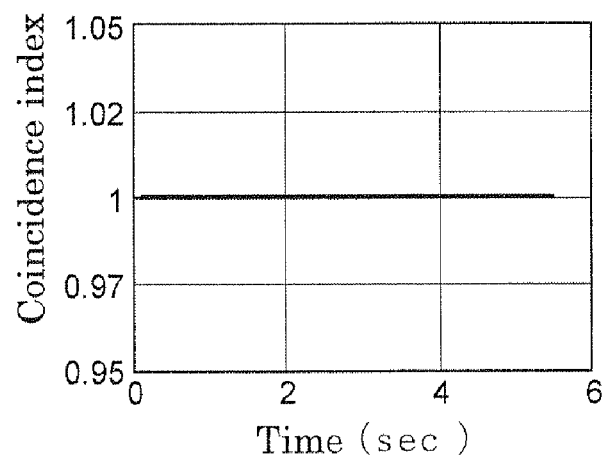
FIG. 19 is a graph showing the coincidence index between the simulation results of FIG. 18 and the theory approximation expression.
Figure 20:
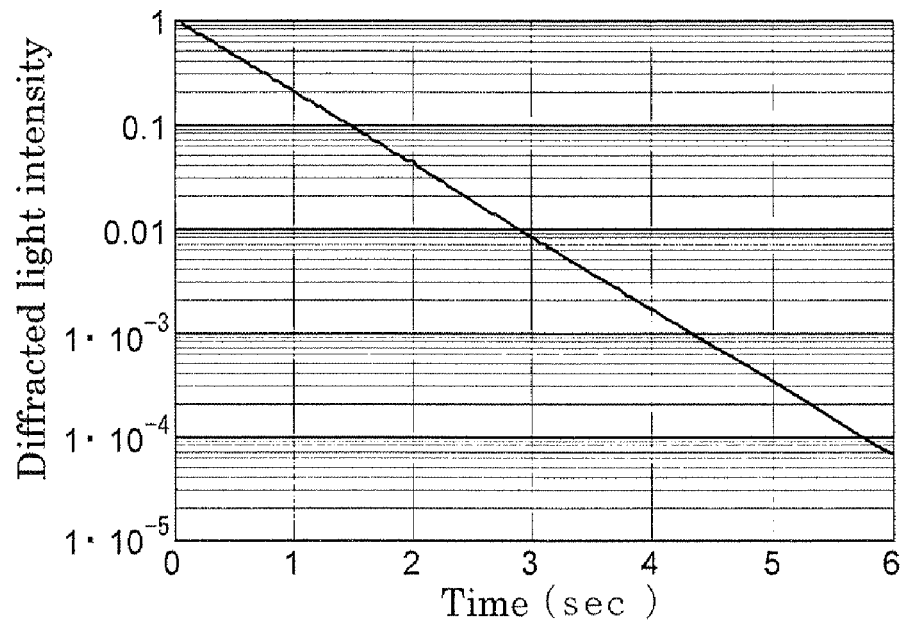
FIG. 20 is a graph showing simulation results of the temporal change in the diffracted light intensity when the particles are freely diffused from the profile of the particle density shown in FIG. 17 to which the electrode pattern shown in FIG. 14 is added.
Figure 21:
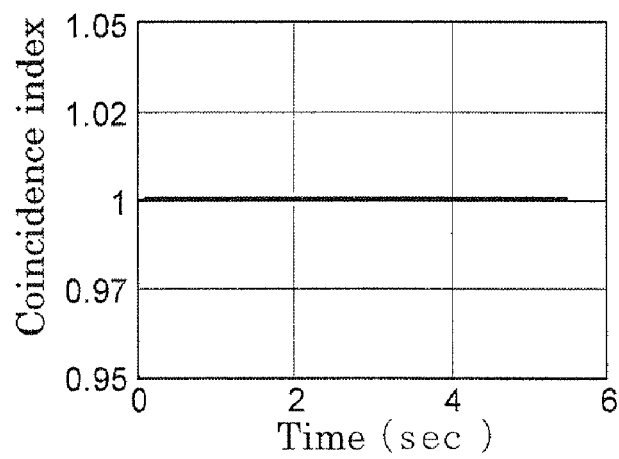
FIG. 21 is a graph showing the coincidence index between the simulation results of FIG. 20 and the theory approximation expression.
Figure 22:
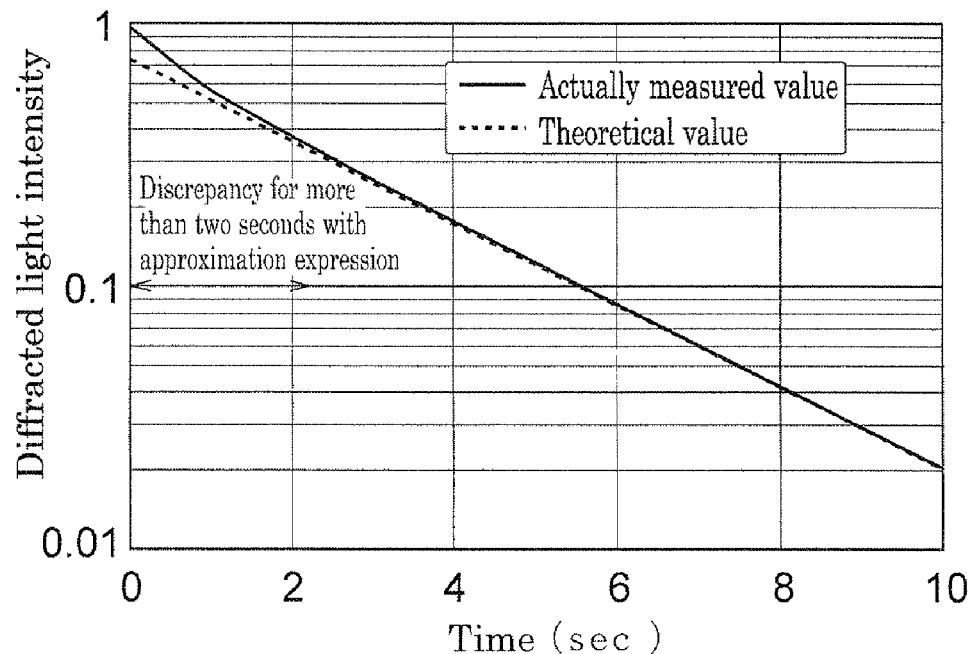
FIG. 22 is a graph showing a measurement result (a solid line) of the temporal change in the diffracted light intensity regarding to polystyrene particles with a diameter of 60 nm by using a conventional electrode pair with width of electrode pieces of 5 μm and a space distance between the electrode pieces of 5 μm, and a calculation value (a broken line) by the theory approximation expression.
Figure 23:
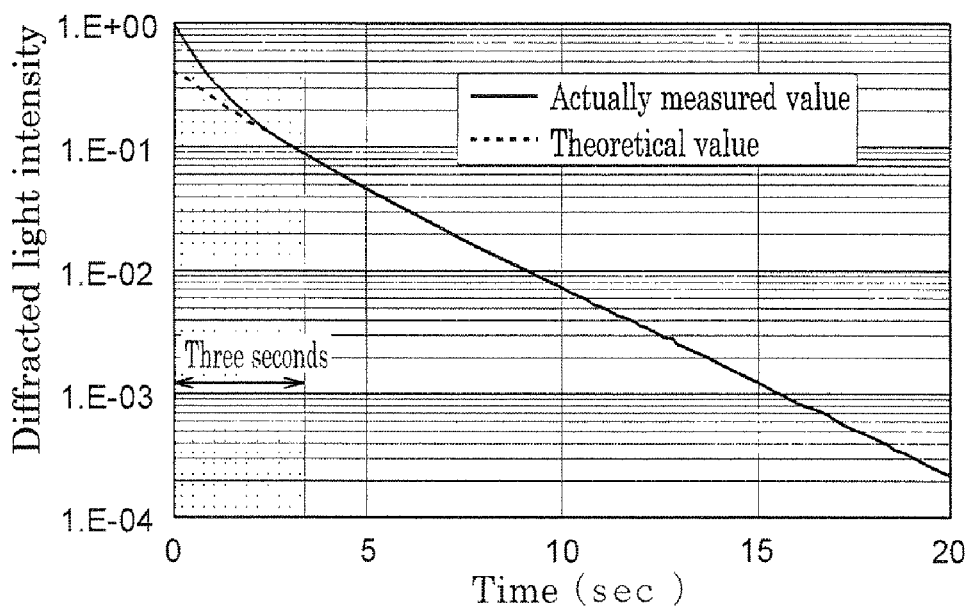
FIG. 23 is a graph showing an actually measured value (a solid line) of the temporal change in the diffracted light intensity in the case where the particles with a diameter of 10 nm is included by an equal amount to the particles with a diameter of 60 nm, and a calculated value (a broken line) obtained by the theory approximation expression in the case where a rate of 0.49 of the particles with a diameter of 60 nm and a rate of 0.16 of the particles with a diameter of 20 nm are included, the attenuation rate of the diffracted light after 3 seconds passes from the start of the diffusion being substantially similar for both the values.

From FIG. 8, the analytical result shows the particle size distribution having two peaks in particle size of 6 to 7 µm and 18 to 20 µm, and quasi-peaks of the particle size are not shown. Thus, an effect of the electrode pair with $L/(L+S) \leqq 0.3$ is obtained.

Industrial Applicability

According to the present invention, the generation of steep attenuation of the diffracted light at the initial stage of the diffusion of the particles due to a structure of the measurement apparatus can be suppressed. As a result, even with the sample in which the measured particles having a plurality of size are mixed such as polydisperse system particles, the particle size distribution can be accurately measured.

The invention claimed is:

1. An optical measurement apparatus, comprising:
  a container for storing a sample having particles dispersed movably in a medium;
  a power source for generating an AC or DC voltage;
  an electrode pair for generating an electric field having a space period in the container by application of the voltage from the power source;
  an irradiation optical system for applying a parallel light flux to a diffraction grating resulting from density distribution of the particles generated in the container by the application of the voltage;
  a detection optical system for detecting diffracted light generated from the parallel light flux passing through the diffraction grating;
  voltage control means for controlling to generate and annihilate the diffraction grating resulting from the density distribution of the particles in the container by the application of the voltage from the power source to the electrode pair and stoppage and modulation of the application of the voltage; and
  data processing means for taking in outputs of the detection optical system to execute the process of evaluating characteristics of the particles and/or the medium, wherein
  electrodes constituting the electrode pair include multiple mutually parallel linear electrode pieces and a connection part electrically connecting the respective electrode pieces to each other, respectively,
  electrode piece ununiformly-arranged areas including at least two of the linear electrode pieces arranged adjacently to each other, and electrode piece absent areas without the electrode pieces arranged therein are alternately formed in each of the electrodes,
  the electrodes are arranged so that the electrode piece ununiformly-arranged areas of one of the electrodes are positioned in the electrode piece absent areas of the other electrode, and the electrode pieces of the electrodes are in parallel with each other at regular intervals, and
  a relationship between width L of the electrode pieces of each of the electrodes and a space distance S between the electrode pieces is as follows:

$$L/(L+S) \leqq 0.3.$$

2. The electrode pair used for the optical measurement apparatus according to claim 1, wherein
  the electrode pair is formed of a vapor deposition film of a conductive body on a surface of a transparent flat plate.

* * * * *